United States Patent

Bäckström et al.

[11] Patent Number: 5,356,923
[45] Date of Patent: Oct. 18, 1994

[54] 1-HYDROXY-4(3-CYCLOPENTYLOXY-4-METHOXYPHENYL)-2-PYRROLIDONE AND ANTI-HYPERTENSIVE USE THEREOF

[75] Inventors: Reijo Bäckström, Helsinki; Erkki Honkanen; Atso Raasmaja, both of Espoo; Inge-Birtt Linden, Helsinki, all of Finland

[73] Assignee: Orion-yhtymä Oy, Espoo, Finland

[21] Appl. No.: 940,853

[22] PCT Filed: Apr. 26, 1991

[86] PCT No.: PCT/FI91/00123

§ 371 Date: Oct. 22, 1992

§ 102(e) Date: Oct. 22, 1992

[87] PCT Pub. No.: WO91/16303

PCT Pub. Date: Oct. 31, 1991

[30] Foreign Application Priority Data

Apr. 26, 1990 [GB] United Kingdom ............... 9009395

[51] Int. Cl.$^5$ .................. C07D 207/46; A61K 31/40
[52] U.S. Cl. .................................. 514/425; 548/542
[58] Field of Search ........................ 548/542; 514/425

[56] References Cited

U.S. PATENT DOCUMENTS

| | | | |
|---|---|---|---|
| 4,012,495 | 3/1977 | Schmiechen et al. | 424/274 |
| 4,193,926 | 3/1980 | Schmiechen et al. | 260/326.5 |
| 4,738,986 | 4/1988 | Kneen et al. | 514/575 |
| 4,977,188 | 12/1990 | Kneen et al. | 514/575 |

FOREIGN PATENT DOCUMENTS 0196184 10/1986 European Pat. Off.
85404 1/1986 Luxembourg.

OTHER PUBLICATIONS

Michel Cariou et al, J. Electroanal. Chem., "Mechanism of the Electroreduction of Aliphatic Nitro Compounds", vol. 182, 1985, pp. 345–354.

H. Singer et al, Synthesis, "Tetramethylguanidine-Catalyzed Addition of Nitromethane to α, β-Unsaturated Carboxylic Acid Esters", vol. 265, 1971, pp. 44–45.

Primary Examiner—David B. Springer
Attorney, Agent, or Firm—Burns, Doane, Swecker & Mathis

[57] ABSTRACT

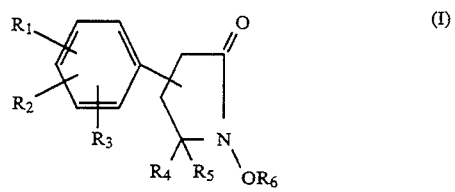

Substituted cyclic hydroxamic acids of general formula (I) in which $R_1$, $R_2$ and $R_3$ are independently hydrogen, halogen, lower alkyl, lower alkoxy, cycloalkoxy, aryloxy which is optionally substituted by 1 to 3 halogen, or aralkyloxy, which is optionally substituted by 1 to 3 halogen, or $R_1$ and $R_2$ together form a —O—CH$_2$—O— group; with the proviso that $R_3$ is not hydrogen when $R_1$ and $R_2$ are both hydrogen; $R_4$ and $R_5$ are independently hydrogen or lower alkyl, $R_6$ is hydrogen or lower alkyl and physiologically acceptable salts and esters thereof are selective inhibitors of phosphodiesterase IV activity and leukotriene $B_4$ and $C_4$ synthesis without showing any significant effect on phosphodiesterase III activity, and are therefore useful in the treatment of hypersensitivity and inflammatory diseases.

4 Claims, No Drawings

1-HYDROXY-4(3-CYCLOPENTYLOXY-4-METHOXYPHENYL)-2-PYRROLIDONE AND ANTI-HYPERTENSIVE USE THEREOF

The present invention relates to new substituted cyclic hydroxamic acids and physiologically acceptable salts and esters thereof. The invention also relates to the pharmaceutical compositions containing these compounds and to the method for the preparation of the same.

The compounds of the present invention are selective inhibitors of phosphodiesterase IV (PDE IV) activity and leukotriene $B_4$ ($LTB_4$) and $C_4$ ($LTC_4$) synthesis without having any significant effect on phosphodiesterase III (PDE III) activity.

The combinatory effect due to the parallel inhibition of PDE IV activity and $LTB_4$ and $LTC_4$ synthesis makes the compounds of the invention especially valuable in the treatment of hypersensitivity and inflammatory diseases such as allergic rhinitis, atopic dermatis, rheumatoid arthritis, psoriasis and especially asthma.

Conventionally, acute asthma has been treated using compounds that aid tracheal relaxation. Because these compounds only treat the acute symptom, other medicaments have to be given that treat pathogenic factors of the disease. These medicaments are, for example, compounds having antiinflammatory effect.

It has been surprisingly found that the compounds of the invention provide in one and the same compound three valuable characterictics. Inhibition of PDE IV activation and increase of cyclic AMP concentration leads to the tracheal relaxation, and is effective in acute asthma. On the other hand, the inhibition of the synthesis of $LTC_4$ diminishes bronchoconstriction in asthmatic subjects. At the same time, the inhibition of $LTB_4$ synthesis has a potent antiinflammatory effect and is therefore believed to be effective in chronic asthma.

The compounds according to the present invention are substituted cyclic hydroxamic acids of general formula I

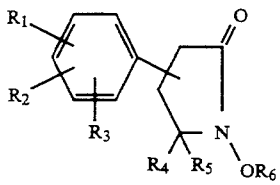

I in which $R_1$, $R_2$ and $R_3$ are independently hydrogen, halogen, lower alkyl, lower alkoxy, cycloalkoxy, aryloxy which is optionally substituted by 1 to 3 halogen, or aralkyloxy, which is optionally substituted by 1 to 3 halogen, or $R_1$ and $R_2$ together form a —O—CH$_2$—O—group; with the proviso that $R_3$ is not hydrogen when $R_1$ and $R_2$ are both hydrogen; $R_4$ and $R_5$ are independently hydrogen or lower alkyl, $R_6$ is hydrogen or lower alkyl, and physiologically acceptable salts and esters thereof.

The term "lower alkyl" as employed herein itself or as a part of another group refers to a straight or branched alkyl group having preferably 1 to 4 carbon atoms.

The term "lower alkoxy" as employed herein refers to an alkyl residue as defined above linked to an oxygen atom.

The term "cycloalkoxy" as employed herein refers to a saturated cyclic hydrocarbon group, preferably of 3 to 7 carbon atoms linked to an oxygen atom.

The term "aryloxy" as employed herein refers to an aromatic ring, preferably phenyl, linked to an oxygen atom.

The term "aralkyloxy" as employed herein refers to a lower alkoxy group having aryl, preferably phenyl, as the substituent.

The term "halogen" as employed herein refers to chlorine, bromine, fluorine or iodine, chlorine and bromine being preferred.

Particularly preferred groups of compounds include those in which $R_1$ is cycloalkyloxy, e.g. cyclopentyloxy, $R_2$ is lower alkoxy, e.g. methoxy or ethoxy, and $R_6$ is hydrogen. The phenyl group in Formula I may be in the 3- or 4-position of the pyrrolidone ring. The 4-position is preferred.

U.S. Pat. No. 4,012,495 describes 4-polyalkoxyphenyl-2-pyrrolidones, such as 4-[3-(cyclopentyloxy)-4-methoxyphenyl]-2-pyrrolidone (rolipram). These compounds are stated to be useful in the treatment of various neurological and psychic disorders. The hydroxamic acids of the invention are chemically different from the compounds of U.S. Pat. No. 4,012,495. Furthermore, the specific compound of U.S. Pat. No. 4,012,495 (rolipram) is not selective PDE IV inhibitor but also inhibits PDE III. PDE III inhibitors are known to be used as inotropic agents in the treatment of heart failure. Therefore, the selective inhibition of only PDE IV in the trachea would be preferred to eliminate cardiac side effects such as arrhytmia the presence of which, it is suggested, is involved in the use of PDE III inhibitors.

The compounds of the formula I may be prepared in accordance with the present invention by selective reduction of the compounds of the formula IIa or IIb

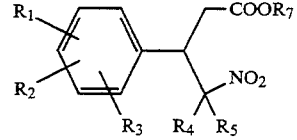

IIa

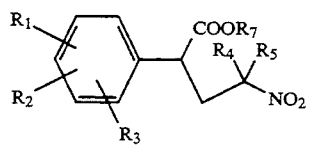

IIb in which $R_1$, $R_2$, $R_3$, $R_4$ and $R_5$ are the same as defined above and $R_7$ represents a lower alkyl group, with zinc dust, aluminium amalgam or sodium borohydride in the presence of platinium or palladium catalyst in a suitable buffer solution or in an inert solvent. Also electrochemical reduction applying the methof described by Cariou M., Hazard R., Jubault M., and Tallec A. in J. Electroanal. Chem. 182 (1985), pp. 345–354 is possible.

The compounds of formula IIa and IIb may be prepared by the known methods (Pollini G. P., Barco A., DeGuili G., Synthesis, (1972), p. 44) from the corresponding cinnamic or 2-phenyl acrylic acid derivatives of formula IIIa and IIIb, respectively

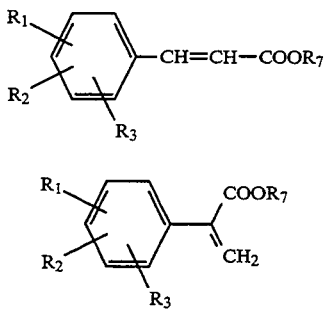

in which $R_1$, $R_2$, $R_3$ and $R_7$ are the same as defined above, by Michael addition reaction of nitroalkane in the presence of a basic catalyst such as 1,1,3,3-tetramethylquanidine by using nitroalkane as the solvent at ambient or elevated temperature.

The compounds of formula I wherein $R_6$ is lower alkyl may be prepared by O-alkylation of the compounds of formula I in which $R_6$ is hydrogen, using lower alkylhalide in basic conditions in an inert solvent such as acetone, N,N-dimethyl-formamide, tetrahydrofuran or N-methylpyrrolidone.

Salts of the compounds of the present invention may be prepared by known methods. Most commonly used physiologically acceptable salts are sodium, potassium, ammonium, calcium and magnesium salts.

The above compounds may be formulated to dosage forms using the principles which are known to those having average skill in the art. The compounds according to this invention are given to a patient as such or in combination with suitable pharmaceutical material in the form of tablets, dragees, capsules, suppositories, emulsions, suspensions or solutions whereby the contents of the active compounds is in the formulation from 1 to 100 weight-%.

Choosing the auxiliary ingredients for the formulation is routine for those of ordinary skill in the art. It is evident that suitable solvents, gel forming ingredients, dispersion forming ingredients, antioxidants, colours etc. are used in a normal way.

It is preferred way to give the compositions enterally. When they are given orally, they may be in the form of tablets, granules, capsules, emulsions, suspensions or solutions.

The effective dose varies considerably depending on location, degree and severity of the disease being treated as well as the age and the genaral conditions of the patient. The effective dose is generally from about to 0,1 to about 10 mg/kg per day, preferably from 0,5 to 5 mg/kg per day for an adult, once a day or divided into two to five doses.

The preparation of the compounds according to the invention are described in detail in the following examples.

EXAMPLE 1

1-Hydroxy-4-(3-cyclopentyloxy-4-methoxyphenyl)-2-pyrrolidone

To a solution containing 10.9 g (0.039 mol) methyl 3-cyclopentyloxy-4-methoxycinnamate in 100 ml of nitromethane 5.5 ml 1,1,3,3-tetramethylguanidine was added gradually at ambient temperature. The solution was stirred overnight after which 400 ml of 2N hydrochloric acid and 100 ml dichloromethane were added. The organic phase was separated and evaporated in vacuo. Yield 13.0 g (100%), a yellowish oil which crystallized on standing.

A solution containing 13.0 g (0.039 mol) methyl 3-(3-cyclopentyloxy-4-methoxyphenyl)-4-nitrobutanoate prepared above in 400 ml tetrahydrofuran containing 4 ml water was gradually added to 3.8 g aluminium foil treated before with a solution of mercuric chloride (1 g) in water. The temperature was held at 15°–20° C. by cooling. The mixture was stirred overnight at ambient temperature after which toluene and 200 ml 6N hydrochloric acid were added. The organic phase was separated and washed with 0.8M sodium hydrogen carbonate solution and evaporated to dryness in vacuo. The residue was crystallized from a mixture of dichloromethane-ether. Yield 1.7 g (15 mp 126°–130° C.

EXAMPLE 2

4-(4-Benzyloxyphenyl)-1-hydroxy-2-pyrrolidone

The starting material methyl 3-(4-benzyloxyphenyl)-4-nitrobutanoate was obtained by condensation of methyl 4-benzyloxycinnamate with nitromethane, yield about 100% or a yellowish oil.

5.0 g of methyl 3-(4-benzyloxyphenyl)-4-nitrobutanoate was reduced in a similar manner as described in Example 1 to yield 0.3 g 4-(4-Benzyloxyphenyl)-1-hydroxy-2-pyrrolidone, mp 150°–155° C.

EXAMPLE 3

4-(4-Benzyloxyphenyl)-1-methoxy-2-pyrrolidone

A mixture containing 0.7 g 4-(4-benzyloxyphenyl)1-hydroxy2-pyrrolidone (Example 2), 5.0 ml methyl iodide and 2.0 g potassium carbonate in 5.0 ml N-methylpyrrolidone was stirred for 2 h at 50° C. 20 ml 1N sodium hydroxide solution was then added and the solution was extracted with a mixture of 20 ml cyclohexane and 10 ml of ether. The extract was washed with water and concentrated in vacuo whereupon the product crystallized. yield 0.31 g (41%), mp 92°–97° C.

EXAMPLE 4

4-(2,3-Dimethoxyphenyl)-1-hydroxy-2-pyrrotidone potassium salt

The starting material methyl 3-(2,3-dimethoxyphenyl)nitrobutanoate was obtained by condensation of methyl 2,3-dimethoxycinnamate with nitromethane, yield about 100% of a yellowish oil.

16.0 g methyl 3-(2,3-dimethoxyphenyl)-4-nitrobutanoaze was reduced in a similar manner as described in Example 1. The crude product was dissolved in 50 ml of anhydrous ethanol and 45 ml of 0.5N potassium hydroxide in ethanol, after which 100 ml ether was added. The potassium salt precipitated was filtered. Yield 3.66 g (25%), mp 138°–143° C.

EXAMPLE 5

4 -[3 -(2,6-Dichlorobenzyloxy) -4-methoxyphenyl]-1-hydroxy-2-pyrrolidone

The starting material methyl 3-[3-(2,6-dichlorobenzyloxy)-4-methoxyphenyl]-4-nitrobutanoate was obtained in a similar way as described in foregoing Examples. Yield about 100% of a yellowish oil.

21.5 g of methyl 3-[3-(2,6-dichlorobenzyloxy)4-methoxyphenyl]-4-nitrobutanoate was reduced as described in Example 1. Yield 7.4 g (39%), mp 134°–140° C.

EXAMPLE 6

1-Hydroxy-4-(3,4-methylenedioxyphenyl)-2-pyrrolidone

The starting material methyl 3-(3,4-methylenedioxyphenyl)-4-nitro butanoate was obtained by condensation of methyl 3,4-methylenedioxycinnamate with nitromethane, yield about 100% of a yellowish oil.

12.0 g of methyl 3,4-methylenedioxy-4-nitrobutanoate was reduced in a similar manner as described in Example 1. The crude product was crystallized from methanol-water. Yield 0.9 g, mp 119°–123° C.

EXAMPLE 7

1-Hydroxy-4-(3,5-di-tert.butyl-4-methoxyphenyl)-2-pyrrolidone

The starting material methyl 3-(3,5-di-tert.-butyl-4-methoxyphenyl)-4-nitrobutanoate was obtained by condensation of methyl 3,5-di-tert.-butyl-4-methoxycinnamate with nitromethane, yield about 100% of a yellowish oil.

8.3 g of methyl 3-(3,5-di-tert.-butyl-4-methoxyphenyl)-4-nitrobutanoate was reduced in a similar manner as described in Example 1. The crude product was crystallized from methanol-water, yield 0.35 g, mp 196°–200° C.

EXAMPLE 8

1-Hydroxy-4-(2,4-dichlorophenyl)-2-pyrrolidone

The starting material methyl 3-(2,4-dichlorophenyl)-4-nitrobutanoate was prepaded in the usual way from methyl 2,4-dichlorocinnamate and nitromethane in about theoretical yield.

16.0 g of methyl 3-(2,4-dichlorophenyl)-4-nitrobutanoate was reduced with aluminium amalgam as described in Example 1. The crude product was crystallized from toluene, yield 2.78 g, mp 153°–156° C.

EXAMPLE 9

1-Hydroxy-4-(2,4-dichlorophenyl)-5-methyl-2-pyrrolidone

The starting material methyl 3-(2,4-dichlorophenyt-4-nitropentanoate was prepared in the usual way from methyl 2,4-dichlorocinnamate and nitroethane in about theoretical yield.

16.0 g of methyl 3-(2,4-dichlorophenyl)-4-nitropentanoate was reduced with aluminium amalgam as described in Example 1. The crude product was crystallized from dioxanecyclohexane. Yield 1.7 g of a mixture of diastereomers, mp 140°–144° C.

EXAMPLE 10

1-hydroxy-4-(2,4-dichlorophenyl)-5,5-dimethyl-2-pyrrolidone

The starting material methyl 3-(2,4-diclorophenyl)-5-methyl4-nitropentanoate was prepared in the usual way from methyl 2,4-dichlorocinnamate and 2-nitropropane in about theoretical yield.

16.0 g of methyl 3-(2,4-dichlorophenyl)-5-methyl-4-nitropentanoate was reduced with aluminium amalgam as described in Example 1. The crude product was crystallized from methanol, yield 4.9 g, mp 234°–237° C.

EXAMPLE 11

1-Hydroxy-5,5-dimethyl-4-(3,4-methylenedioxyphenyl)-2-pyrrolidone

The starting material methyl 3-(3,4-methylenedioxyphenyl)-5-methyl-4-nitropentanoate was prepared in the usual way from methyl 3,4-methylenedioxy cinnamate and 2-nitropropane in about theoretical yield.

16.0 g methyl 3-(3,4-methylenedioxyphenyl)-5-methyl-4-nitropentanoate was reduced with aluminium amalgam as described in Example 1. The crude product was crystallized from toluene, yield 3.8 g, mp 185°–189° C.

EXAMPLE 12

1-Hydroxy-5,5-dimethyl-3-(3-chlorophenyl)-2-pyrrolidone

The starting material methyl 2-(3-chlorophenyl)-4-methyl-4-nitropentanoate was obtained by condensation of methyl 2-(3-chlorophenyl)acrylate with 2-nitropropane, yield about 100% of yellow oil. 18.95 g of methyl 2-(3-chlorophenyl)-4-methyl-4-nitropentanoate was reduced with aluminium amalgam as described in Example 1. The crude product was crystallized from toluene-ether, yield 2.5 g, mp 160°–162° C.

Inhibition of PDE IV and PDE III

PDE isoenzymes were isolated using DEAE-Sepharose chromatography as described by Reeves et al. in Biochem. J., 241 (1987), pp. 535–541. PDE IV and PDE III activities were determined by the method of Alajoutsijärvi and Nissinen as described in Anal. Biochem. 165 (1987), pp. 128–132.

TABLE 1

| The selectivity of the inhibition of PDE IV and PDE III of the test compound. | | |
|---|---|---|
| Compound of Example | $IC_{50}$ PDE IV $\mu M$ | PDE III $\mu M$ |
| 1 | 0,9 | 205 |
| Test compound 1-hydroxy-4-(3-cyclopentyloxy-4-methoxyphenyl)-2-pyrrolidone | | |

Inhibition of $LTB_4$ synthesis and $LTC_4$ synthesis

The inhibition of arachidonic acid induced $LTB_4$ and $LTC_4$ synthesis in human basophilic leucocytes was determined with liquid chromatography and UV detection. $LTB_4$ and $LTC_4$ were separated first by HPLC with a Spherisorb ODS colon (5 $\mu m$, 150×4.6 mm) and Spectroflow 400 Kratos Analytical pump. The flow rate was 1 ml/min and the solvents were methanol/water/acetic acid (68132/0.1), pH 5.0 for $LTB_4$ and methanol/water/acetic acid/phosphoric acid (65/35/0.07/0.03), pH 5.5 for $LTC_4$. The peaks were analyzed further with Spektroflow 773 Kratos Analytical UV absorbance detector and leukotrienes were detected at the wavelength of 271 nm and 280 nm for $LTB_4$ and $LTC_4$, respectively.

The results are given in Table 2

TABLE 2

| The $LTB_4$ and $LTC_4$ synthesis inhibition | | |
|---|---|---|
| The compound of the Example | $IC_{50}$ $LTB_4$ $\mu M$ | $IC_{50}$ $LTC_4$ $\mu M$ |
| 1 | 3.7 | 3.2 |

We claim:

1. 1-Hydroxy-4-(3-cyclopentyloxy-4-methoxyphenyl)-2-pyrrolidone.

2. A pharmaceutical composition for use in the treatment of hypersensitivity or inflammatory disease, said composition comprising an effective hypersensitivity-reducing or anti-inflammatory amount of the compound according to claim 1 and a pharmaceutically acceptable carrier or diluent therefor.

3. A method for the treatment of hypersensitivity or inflammatory disease in an animal in need of such treatment, said method comprising administering to said animal an effective hypersensitivity-reducing or anti-inflammatory amount of the compound according to claim 1.

4. The method according to claim 3, wherein the disease is asthma.

* * * * *